United States Patent
San et al.

(10) Patent No.: US 10,752,925 B2
(45) Date of Patent: Aug. 25, 2020

(54) MICROBIAL PRODUCTION OF SUCCINATE DERIVED PRODUCTS

(71) Applicant: WILLIAM MARSH RICE UNIVERSITY, Houston, TX (US)

(72) Inventors: Ka-Yiu San, Houston, TX (US); George N. Bennett, Houston, TX (US); Irene Martinez, Houston, TX (US)

(73) Assignee: William Marsh Rice University, Houston, TX (US)

( * ) Notice: Subject to any disclaimer, the term of this patent is extended or adjusted under 35 U.S.C. 154(b) by 0 days.

(21) Appl. No.: 16/015,101

(22) Filed: Jun. 21, 2018

(65) Prior Publication Data

US 2018/0371508 A1 Dec. 27, 2018

Related U.S. Application Data

(60) Provisional application No. 62/523,595, filed on Jun. 22, 2017.

(51) Int. Cl.
*C12P 7/46* (2006.01)
*C12N 9/88* (2006.01)

(52) U.S. Cl.
CPC .......... *C12P 7/46* (2013.01); *C12N 9/88* (2013.01); *C12Y 402/01002* (2013.01); *C12Y 604/01001* (2013.01)

(58) Field of Classification Search
CPC .......... C12P 7/46; C12Y 604/01001; C12Y 102/01024; C12Y 203/010008; C12Y 207/02001
See application file for complete search history.

(56) References Cited

FOREIGN PATENT DOCUMENTS

WO WO2006031156 * 3/2006

OTHER PUBLICATIONS

Yim et al. 2011; Metabolic engineering of *Eschericha coli* for direct production of 1,4-butanediol. Nature Chemical Biology. 7: 445-452.*

* cited by examiner

*Primary Examiner* — Karen Cochrane Carlson
(74) *Attorney, Agent, or Firm* — Boulware & Valoir

(57) ABSTRACT

Microbes and methods used to convert renewable carbon sources such as glucose, sucrose, biomass hydrolysate, methanol or formate, to succinate-derived products, such as fumarate or malate, which are desirable products having many uses.

7 Claims, 6 Drawing Sheets

MICROBIAL PRODUCTION OF SUCCINATE DERIVED PRODUCTS

PRIOR RELATED APPLICATIONS

This application claims priority to U.S. Provisional Application No. 62/523,595, filed Jun. 22, 2017, and incorporated by reference in its entirety for all purposes.

FEDERALLY SPONSORED RESEARCH STATEMENT

This invention was made with government support under GM090152 awarded by National Institutes of Health ("NIH") and CBET-0828516 awarded by National Science Foundation ("NSF"). The government has certain rights in the invention.

FIELD OF THE DISCLOSURE

The invention relates to microbial production of products using genetically engineered bacteria. In particular, we use high yield succinate production strains/processes to produce succinate-derived products. We have shown that succinic acid biosynthesis can be achieved at high yield and high rate (actually fixing carbon dioxide during the synthesis process), as such, succinate derived products will also have a high carbon yield advantage.

BACKGROUND OF THE DISCLOSURE

This invention focuses on the microbial production of succinate, and products derived from succinate.

SUMMARY OF THE INVENTION

The development of biological processes to produce useful compounds from renewable resources has attracted significant interest recently. The current invention exploits a highly efficient succinic acid production process from renewable carbon source using metabolically engineered microorganisms. In addition, this anaerobic succinic acid production process fixes carbon dioxide. $CO_2$ fixation occurs by PYC or PEPC from phosphoenolpyryvate to oxaloacetate, described previously (Sanchez 2005A, 2005B, 2006).

It is envisioned that a process using succinic acid as a precursor to produce various succinic acid derived products (see FIGS. 1-6) will be highly advantageous from the carbon yield point of view, since a major cost factor for most bio-manufacturing processes is the feedstock cost. Examples of succinic acid-derived products are fumarate, malate, aspartate, beta-alanine, quinolinic acid, epoxysuccinate, tartrate, etc.

Experiments were performed to demonstrate the concept of producing malate from glucose via the anaerobic production succinate. The strain SBS550MG-Cms243 pHL413-Km (an *E. coli* derivative carrying a pyruvate carboxylase gene) was used. Succinic acid was first produced anaerobically in the first 24 hours from glucose (FIG. 2). Approximately 180 mM of succinic acid was produced from about 100 mM of glucose. This succinic acid yield is very close to the maximum theoretical yield with the incorporation of carbon dioxide. At 24 h, the process was switched to aerobic conditions, at which time the succinic acid was converted to malic acid by the same strain. This strain produced 133 mM malate in 47 h, with a high yield of 1.3 mole (mole glucose)$^{-1}$.

1A: Conversion of Succinate to Fumarate

Experiments were performed to demonstrate the concept of aerobic production of fumarate from succinate. Four strains were constructed and their ability and performance to carry out such a conversion was tested. These four strains had reduction of expression of ldhA, and adhE and various combinations of deletions of the various fumerases—fumA, fumB, and fumC.

The strains are MBS406: MG1655 ΔldhA ΔadhE ΔfumAC::Cm; MBS426: MG1655 ΔldhA ΔadhE ΔfumB ΔfumAC::Km; MBS410: MG1655 ΔldhA ΔadhE ΔfumA:: Km; MBS412: MG1655 ΔldhA ΔfumA ΔfumB::Km; MBS420: MG1655 ΔldhA ΔadhE ΔfumB::Km; MBS432: S MG1655 ΔldhA ΔadhE ΔfumC ΔfumB::Km; MBS440: MG1655 Δmdh.

Fumarase (or fumarate hydratase) is an enzyme that catalyzes the reversible hydration/dehydration of fumarate to malate. With reduction in activity, more fumarate accumulates in the strain.

The fumAC deletion mutant strains showed the highest fumarate production, 69.37 and 29.88 mM for MBS406 and MBS426, respectively. Fumarate yields were close to stoichiometric (0.86 and 0.93 mol/mol succinate, respectively) when succinate was used as a precursor in aerobic conditions (Table below). The inactivation of fumA and fumC led to the accumulation of fumarate instead of malate, consistent with literature report that fumA and fumC are the main fumarases in aerobic conditions. The strain MBS406 (a fumAC deletion mutant) has a faster conversion rate and produced more fumarate, but with a slightly lower yield. A small quantity of malate was also detected due to the presence of FumB. On the other hand, the strain MBS426 with both fumB and fumAC inactivation showed a higher yield (no detectable malate), but with a slower conversion rate.

In summary, it is feasible to produce fumarate at high yields using succinate as the intermediate. The maximum theoretical molar yield of fumarate from glucose is 1.72 mole fumarate/mole glucose (since the maximum molar succinate yield from glucose is 1.72 (mole succinate per mole glucose); the maximum molar fumarate yield from succinate is 1.0. In this example, potentially the fumarate yield achievable can be 1.58 (=1.7*0.93) using a molar succinate yield of 1.7 from glucose, which we have demonstrated in Experiment 1a. This high yield value has never been reported in the literature. See FIGS. 3A and 3B.

2: Prophetic Succinic Acid Derived Products

A number of other compounds can be made from succinate by engineered microorganisms. The advantage of forming the compound from succinate is a higher yield than can be obtained directly from glucose, since succinate is made with a molar yield of more than 1.6 from glucose by our previous patented procedures, incorporated by reference herein their entirety for all purposes.

2A. Aspartic Acid Via Succinic Acid

One of the most useful pathways would be from succinate to the amino acid, aspartic acid. This would be done as with the malate example. However, once fumarate is formed by succinate dehydrogenase EC 1.3.5.1 or fumarate reductase EC 1.3.1.6, instead of going to malate, the fumarate is converted to aspartic acid as seen in FIG. 4. This formation of aspartic acid from fumarate is a widely known reaction catalyzed by aspartase EC 4.3.1.1, and is used for in vitro formation of aspartate from fumarate. Bioconversion of fumaric acid to aspartic acid from fumaric acid mediated by the activity of aspartate ammonia-lyase (aspartase) has been demonstrated.

Strains with usual activity of fumarase, which converts fumarate to malate, could be blocked by use of a labile mutant enzyme, inhibitor or deactivation of the fumarase enzyme by a protease or destabilizing condition. In addition, aspartate ammonia-lyase (aspartase) will be overexpressed in the same strain. After anaerobic succinic acid production from carbon feedstock, the culture will be switched to aerobic condition by bubbling air together with the addition of ammonia. The formation of aspartic acid will be measured e.g., by HPLC.

2B. Quinolinic Acid Via Succinic Acid

There are a number of useful commercial products derived from aspartic acid in the cell. Among those are quinolinic acid, a precursor of niacin, and beta-alanine, a food and pharmaceutical component. Quinolinic acid would be derived from aspartic acid by NadA (EC 2.5.1.72) and NadB (EC 1.4.3.16) action. Beta-alanine can be derived in a one-step decarboxylation reaction of aspartic acid by aspartic acid 1-decarboxylase, panD (EC 4.1.1.11). The genes encoding these enzymes are already known in *E. coli* and many other organisms. FIG. 5.

Strains with usual activity of fumarase, which converts fumarate to malate, could be blocked by use of a labile mutant enzyme, inhibitor or deactivation of the fumarase enzyme by a protease or destabilizing condition. By using a temperature sensitive mutant, for example, the fumarase can be turned off when needed.

For quinolinic acid production, NadA and NadB will be overexpressed in the same strain. After anaerobic succinic acid production from carbon feedstock, the culture will be switched to aerobic condition by bubbling air. The formation of quinolinic acid will be measured e.g., by HPLC.

Similarly, for beta-alanine production, PanD will be overexpressed in the same strain. After anaerobic succinic acid production from carbon feedstock, the culture will be switched to aerobic condition by bubbling air through the culture medium and/or stirring or combinations thereof. The formation of beta-alanine will be measured e.g., by HPLC.

2C. Epdxysuccinate And Tartaric Acid Via Succinic Acid

Another product derived from fumarate is epoxy-succinate, a reactive compound used in polymer formation that is formed by a number of fungi from fumarate. The reaction is catalyzed by an alkene mono-oxygenase described in several organisms that naturally produce epoxysuccinate.

Various filamentous fungi have been reported to accumulate 1-trans-2,3-epoxysuccinic acid (ESA), namely, the basidiomycete *Lentinus degener*, the ascomycete *Byssochlamys nivea*, and the deuteromycetes *Penicillium viniferum* and *Aspergillus fumigatus*.

Epoxysuccinate can be converted easily to tartaric acid by trans-epoxysuccinate hydrolase EC 3.3.2.4, most well studied from *Pseudomonas putida*. Tartaric acid is a valuable compound used in food processing.

Similar to 2B and 2C, strains with usual activity of fumarase, which converts fumarate to malate could be blocked by use of a labile mutant enzyme, inhibitor or deactivation of the fumarase enzyme by a protease or destabilizing condition.

Strains with overexpression of the (enzymes) alkene-mono-oxygenase, and the epoxysuccinate hydrolase will be constructed. After anaerobic succinic acid production from carbon feedstock, the culture will be switched to aerobic condition by bubbling air. The formation of epoxysuccinate and tartaric acid will be measured. These are described specifically below.

For epoxysuccinate acid production, alkene mono-oxygenase from *Aspergillus fumigatus* (Wilkoff 1963) or *Paecilomyces varioti* NRRL 1123 (Ling 1978) will be overexpressed in the same strain. After anaerobic succinic acid production from carbon feedstock, the culture will be switched to aerobic condition by bubbling air. The formation of epoxysuccinate acid will be measured.

For tartaric acid production, alkene mono-oxygenase from *Aspergillus fumigatus* (Wilkoff 1963) or *Paecilomyces varioti* NRRL 1123 (Ling 1978) together with trans-epoxysuccinate hydrolase from *Pseudomonas putida* or *Achromobacter viscosum* will be overexpressed in the same strain. After anaerobic succinic acid production from carbon feedstock, the culture will be switched to aerobic condition by bubbling air. The formation of tartaric acid will be measured.

In addition, succinate can be activated to succinyl-CoA by succinate CoA ligase EC 6.2.1.5, and then converted to a variety of compounds including 1,4-butanediol and gamma-hydroxy-butyrate through reduction reactions. An initial reaction is the formation of succinate semialdehyde by EC 1.2.1.76-succinate-semialdehyde dehydrogenase and then reduction of the aldehyde to the hydroxyl giving 4-hydroxy-butyrate (gamma-hydroxy butyrate) by EC 1.1.1.B47-succinate semialdehyde reductase (NADPH) e.g. from *Metallosphaera sedula* malonic semialdehyde reductase, succinic semialdehyde reductase, and succinyl-coenzyme A reductase from *Metallosphaera sedula*. These are enzymes of the autotrophic 3-hydroxypropionate/4-hydroxybutyrate cycle in *Sulfolobales* (Kockelkorn and Fuchs).

For 4-hydroxy-butyrate production, succinyl-CoA ligase, succinate-semialdehyde dehydrogenase, succinate semialdehyde reductase will be overexpressed in the same strain, as seen in FIG. 6. After anaerobic succinic acid production from carbon feedstock, the culture will be switched to aerobic condition by bubbling air. The formation of 4-hydroxy-butyrate will be measured.

In the last step, the conversion of succinate made and in the broth, to malate there are several avenues to optimize this conversion.

Potential limitations to the conversion efficiency can be addressed by optimization of specific parameters in each case.

1. The desired product could be degraded once it is made from succinate.

An optional change would be to deactivate the enzymes degrading the product, e.g., by inactivating or at least reducing the expression of the gene encoding the enzyme in the host. This would not affect the production of succinate or the conversion steps but would increase final yield of the conversion. Also, a temperature sensitive or other condition for inactivation of the degrading enzyme could be used, such as in the malate example a temperature sensitive malate dehydrogenase could be employed that would not be active in the succinate conversion if the conversion step was done at higher temperature, and this would lessen the degradation of the desired product, malate. For example, the enzyme in *R vannielii* is unstable with a half-life about 8 min at 40 degrees, and in *Rhodobacter capsulatus* the half-life is about 20 min at 40 degrees (Tayeh, 1988).

Another potential improvement is to increase the succinate to malate conversion by overexpressing succinate dehydrogenase and/or one of the fumarases. For the conversion of succinate to fumarate, conditional deactivation of the fumarases needed to be constructed to prevent the undesirable conversion of fumarate to malate. For example, Shibata, 1985, reported low stability of *Euglena* fumarase.

For the conversion of succinate to fumarate, conditional deactivation of the fumarases needed to be constructed to prevent the undesirable conversion of fumarate to malate.

2. The normal *E. coli* or host enzyme(s) for the conversion of succinate to the desired product may not be optimal for the most rapid conversion.

It may be desired to have the conversion go at the most rapid rate, and enzyme(s) from other organisms or mutant enzymes could be used that would have better performance, e.g., an enzyme from a thermophilic organism or an enzyme with better kinetic parameters, either from another organism or one that has been modified by mutation or protein engineering to have improved performance compared to the native host enzyme. This modification also would include changes where the enzymes of the pathway from succinate to product are over expressed.

3. The fate of intermediates of the conversion of succinate to product C may limit conversion efficiency. The conversion of succinate to product C may go through some intermediates, and there may be other active enzymes in the cell that could divert these to other undesired substances. In this case, the competing pathways for intermediates of the pathway from succinate to products could be inactivated by mutation or using a conditionally active enzyme. If that step is needed for some other cell function during the preparation of the cells for the conversion step, the enzyme catalyzing that competing reaction could then be inactivated, e.g., by temperature or cell incubation condition.

4. The cell energetics, transport of the succinate or product, or availability of other substrates of reactions of the pathway for conversion of succinate to product may limit the rate and efficiency of the conversion.

In the formation of the product from succinate, there may be cases where the uptake of succinate or the efflux of product may be limiting and the introduction of higher levels of the appropriate transporters would be beneficial for efficiency. The cell energy or availability of other cofactors, substrates or components that are needed in the biosynthetic pathway of the product from succinate may be limiting and must be added to the media, e.g., ammonia if an amino acid is being made, or a source of energy is needed for certain reactions in which case an energy or redox supplying reaction and substrate could be introduced, e.g., formate and formate dehydrogenase coupled to NADH production could provide energy and redox for various enzyme reactions. Also, the addition of other preformed substances (or precursors of such substances) could be added in the media and then react with the succinate or intermediates of the pathway to product, to give the product or enable the product to be made more efficiently or economically.

The advantages of the innovation are:

Higher yield formation from succinate as an intermediate than from glucose directly.

The ability to use the same cells to perform a two phase reaction with phase one being the formation of succinic acid and the next phase being the subsequent conversion of succinic acid to the desired product.

Alternatively, a mixed culture can be used to carry out the overall conversion process. One strain is designed to carry out the formation of succinic acid and the other strain is optimized to carry out the subsequent conversion of succinic acid in situ to the desired product.

Another advantage is that this biological approach does not require the purification of the succinic acid formed; this is because enzymatic reactions are in general more substrate specific and hence the second conversion step can be carried out directly from the broth containing the succinic acid.

DETAILED DESCRIPTION

Figure 1:
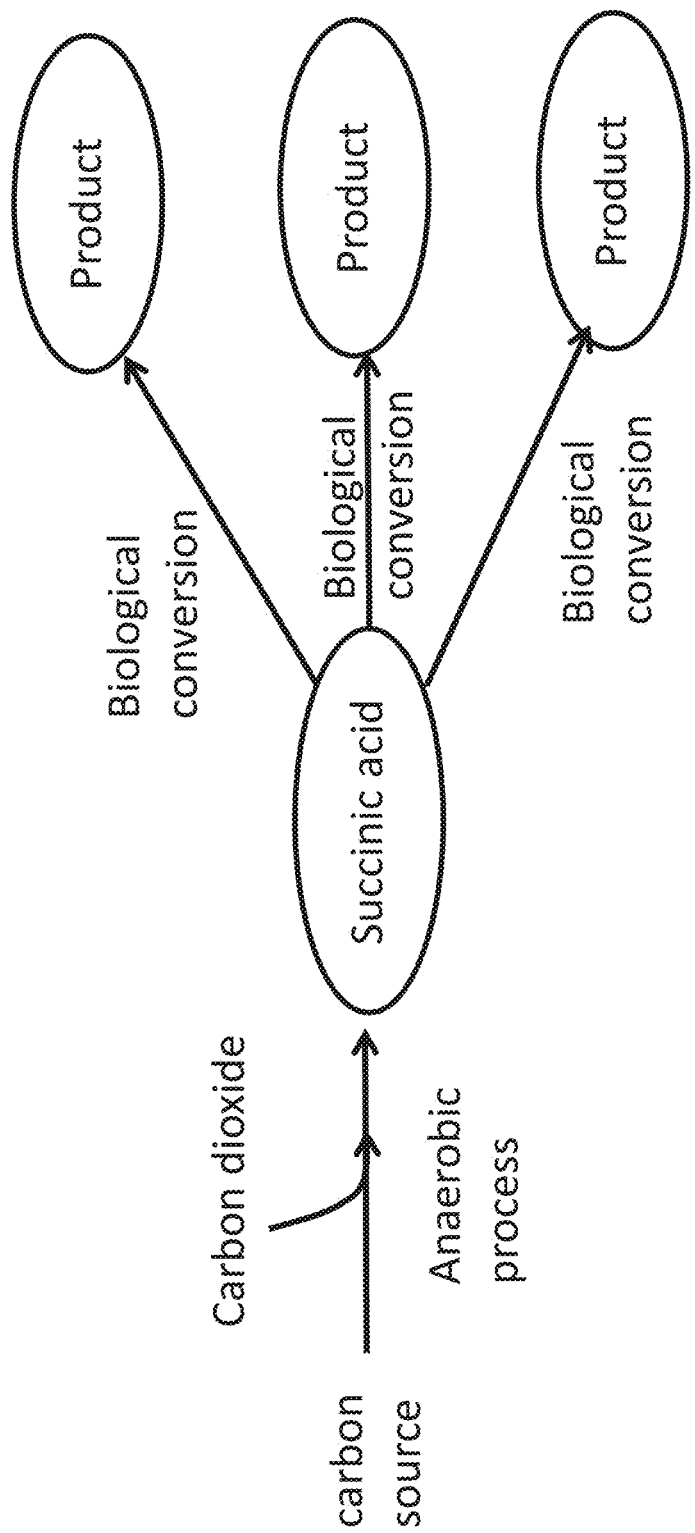
FIG. 1 is a schematic showing production of succinic acid derived products.
Figure 2:
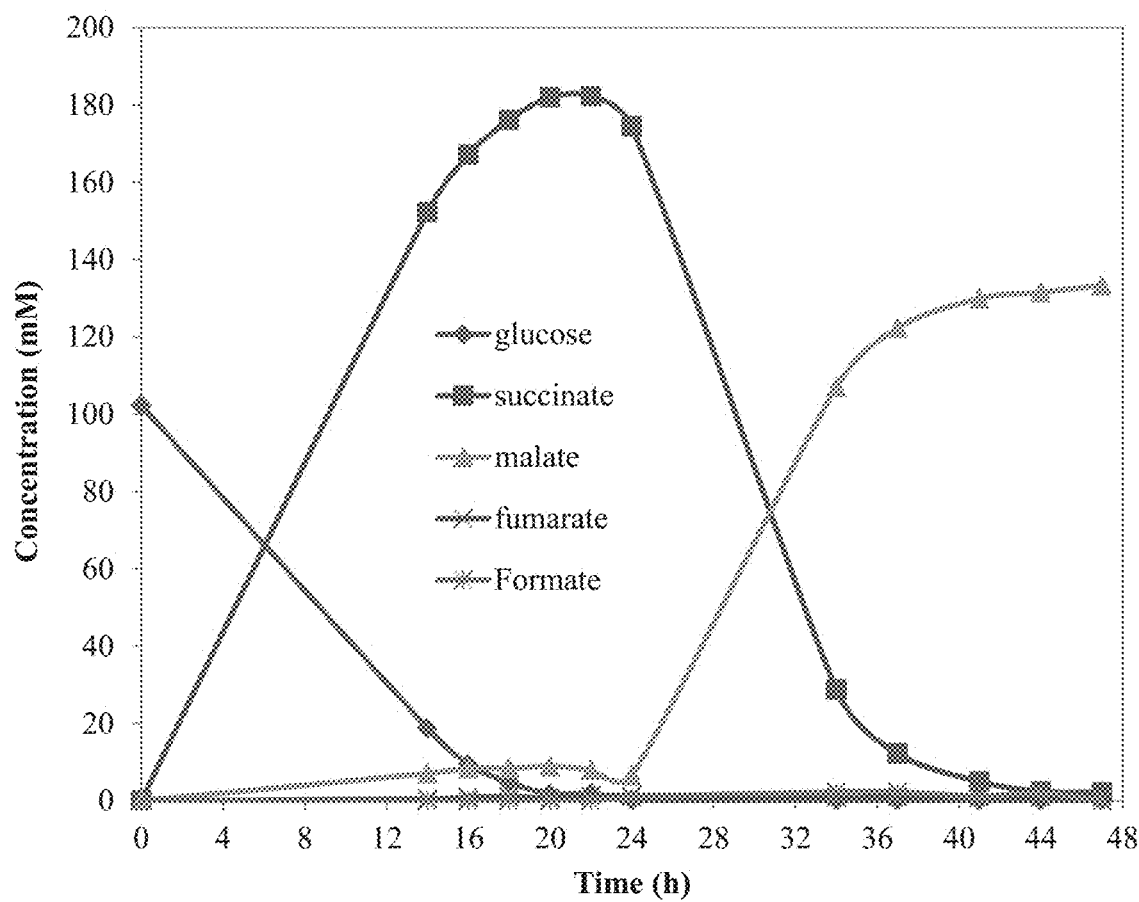
FIG. 2 is a plot showing production of C4-dicarboxylic acids in a two-stage production process using SBS550MG-Cms243 pHL413-Km *E. coli* strain. The first production stage (0-24 h) was anaerobic for glucose conversion into succinate, and the second stage was aerobic for succinate conversion into malate.
Figure 3A:
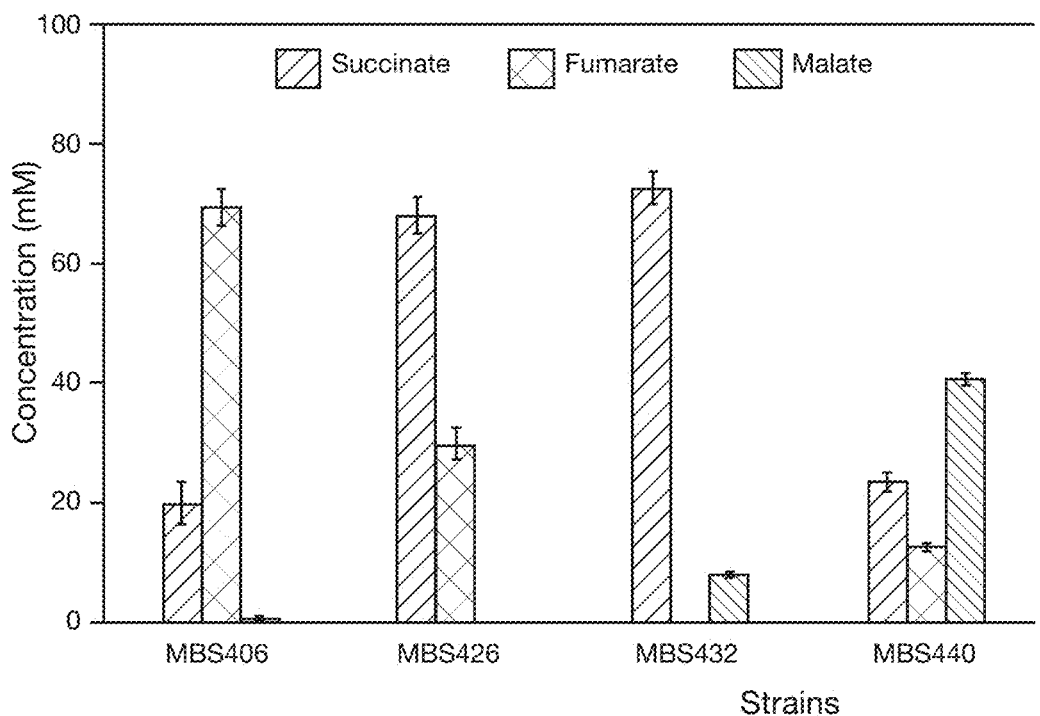
FIG. 3A is a bar graph showing production of succinate, fumarate, and malate by concentration.
Figure 3B:
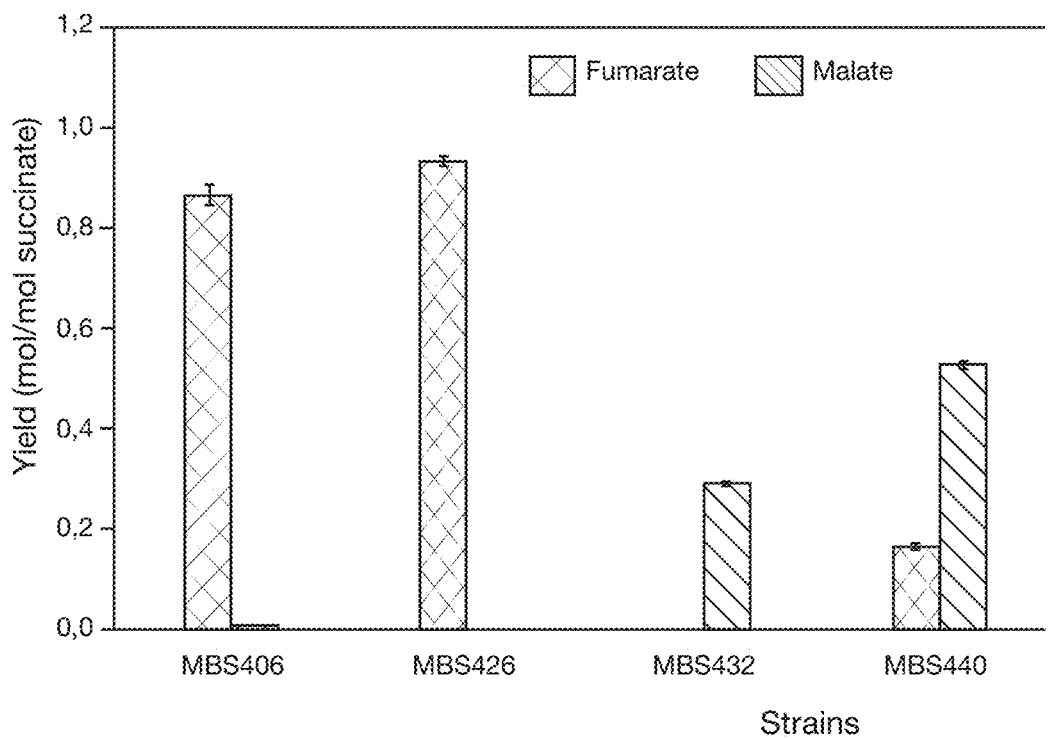
FIG. 3B is a bar graph showing production of succinate, fumarate, and malate by molar yield.
Figure 4:
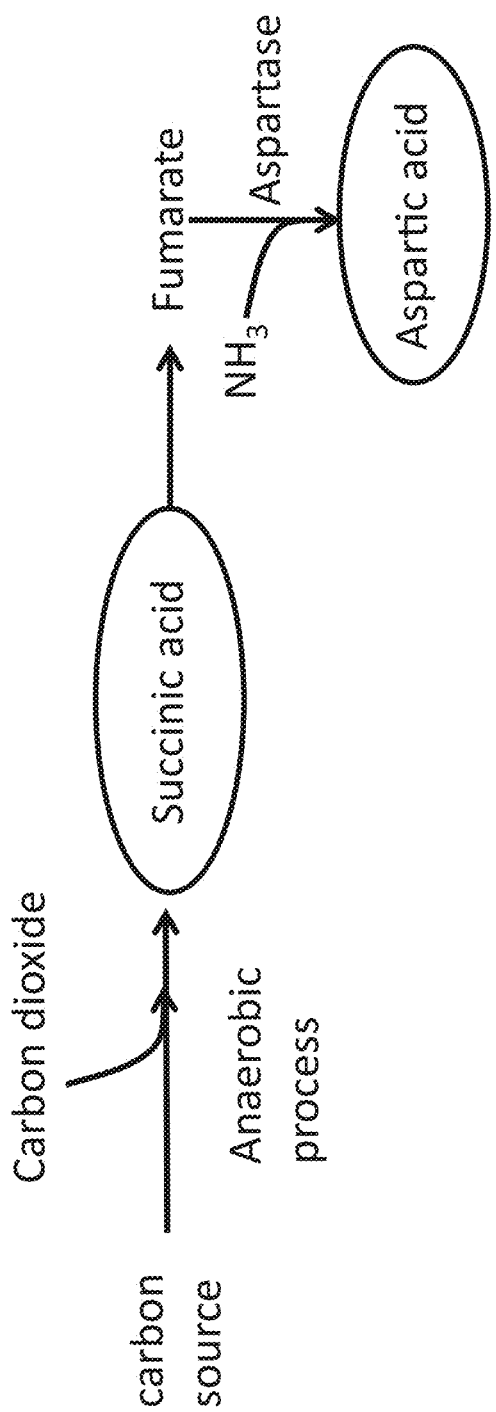
FIG. 4 is a schematic showing production of aspartic acid (aspartate).
Figure 5:
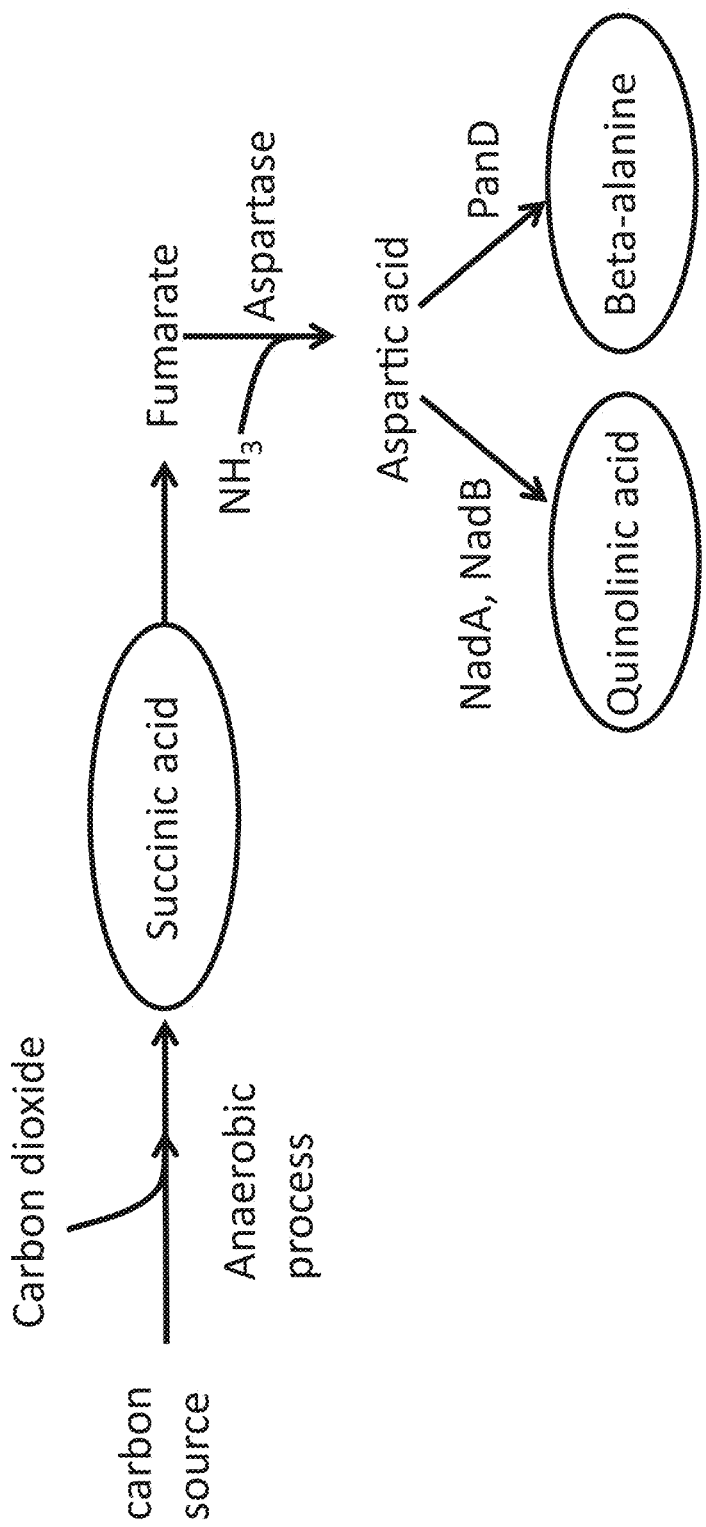
FIG. 5 is a schematic showing production of beta alanine and quinolinic acid.
Figure 6:
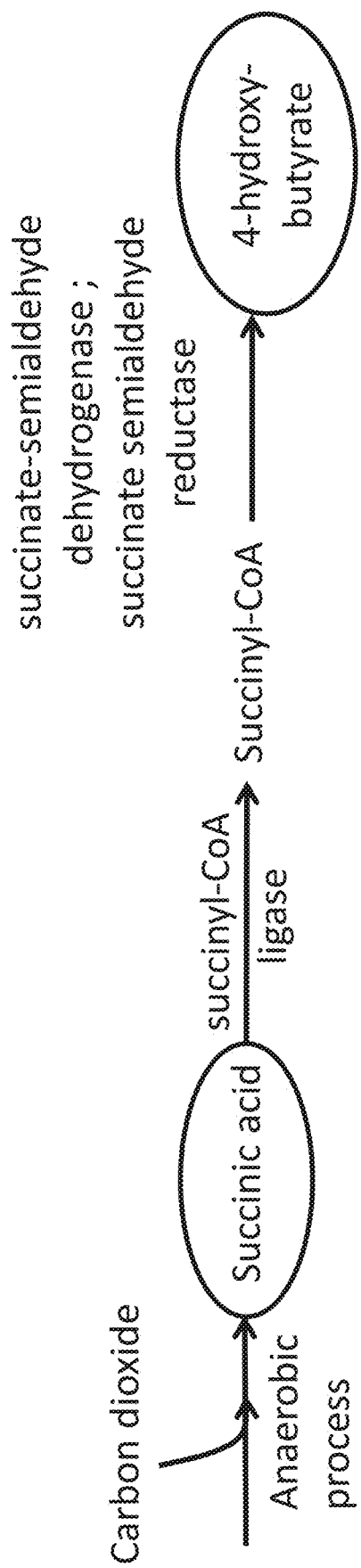
FIG. 6 is a schematic showing production of hydroxy butyrate.

Relevant plasmid constructs were transformed into the *E. coli* mutant strain, e.g., SBS550MG, to carry out certain exemplary embodiments of the invention.

The transformed bacterial strains and plasmids used in certain embodiments of the invention are set forth in Table 1 below.

A mutant *E. coli* strain, SBS550MG, was created in which the genes encoding lactate dehydrogenase (ldhA), alcohol dehydrogenase (adhE), acetate kinase-phosphotransacetylase (ackA-pta) and the aceBAK operon repressor (iclR) were inactivated by deletion. The mutant strains were constructed using the one-step inactivation method of Datsenko and Wanner (2000). This method first requires the construction of the single mutations using the phage λ Red recombinase, and successive use of this technique can be used on the initial modified strain. Alternatively, P1 phage transduction could then used to combine various mutations into one strain. Each mutation is preferably added to the strain one at a time before the introduction of the next mutation because the kanamycin cassette should be removed at each stage to enable selection of the next mutation.

PCR products of the kanamycin cassette gene flanked by FRT (FLP recognition target) sites and homologous sequences to the gene of interest were made using pKD4 as the template. These PCR products were then transformed into the cells by electroporation (Bio-Rad Gene Pulser) for insertional inactivation of the gene of interest. These transformed cells carry the plasmid pKD46 that expresses the λ Red system (γ, β, exo) for recombination of the PCR product into the chromosome. Once the kanamycin cassette is inserted, it can be removed using the helper plasmid, pCP20 that expresses FLP. The removal of the FRT-flanked kanamycin cassette leaves behind an 84-base pair insertion cassette. At each stage of mutation, experiments were performed to test the intermediate mutant for the effect on metabolite production. Throughout the process of constructing the aerobic succinate production system, a library of different mutants with varying types and numbers of mutations was created. All mutants were also verified with genomic PCR after construction to ensure that the gene of interest had been disrupted.

The strain SBS550MG-Cms243(pHL413-Km) (an E. coli derivative carrying a pyruvate carboxylase gene) was then created, by adding a plasmid pTrc99A encoding Pyruvate carboxylase gene from Lactococcus lactis. Cms243 is chloramphenicol sensitive derivative of the Cm resistant parent SBS550, to remove that marker.

The $NAD^+$-dependent formate dehydrogenase gene (fdh1) of Candida boidinii was coexpressed with Lactococcus lactis pyruvate carboxylase (pycA) under the control of $P_{trc}$ and $P_{pycA}$ promoters in plasmid pHL413KF1. The newly introduced fdh1 converts 1 mol of formate into 1 mol of NADH and $CO_2$. The reengineered strain SBS550MG-Cms243(pHL413KF1) retains the reducing power of formate through an increase in NADH availability.

In anaerobic shake flask fermentations, the parent strain SBS550MG-Cms243(pHL413Km) consumed 99.86 mM glucose and produced 172.38 mM succinate, 16.16 mM formate and 4.42 mM acetate. The FDH bearing strain, SBS550MG-Cms243(pHL413KF1) consumed 98.43 mM glucose and produced 171.80 mM succinate, 1 mM formate and 5.78 mM acetate. Furthermore, external formate supplementation to SBS550MG(pHL413KF1) fermentations resulted in about 6% increase in succinate yields as compared to SBS550MG(pHL413Km). In an anaerobic fed-batch bioreactor process, the average glucose consumption rate, succinate productivity, and byproduct formate concentration of SBS550MG(pHL413Km) was 1.40 g/L/h, 1 g/L/h, and 17 mM, respectively. Whereas, the average glucose consumption rate, succinate productivity and byproduct formate concentration of SBS550MG(pHL413KF1) was 2 g/L/h, 2 g/L/h, 0-3 mM respectively. A high cell density culture of SBS550MG(pHL413KF1) showed further improvement in succinate productivity with a higher glucose consumption rate. Reduced levels of byproduct formate in succinate fermentation broth would provide an opportunity for reducing the cost associated with downstream processing, purification, and waste disposal.

In general, the needed overexpressed enzymes are added to the microbe so that the desired pathways can be run. Preferably, the enzymes are added by adding the requisite gene under the control of an inducible promoter, and the genes can be contained on an expression vector, or integrated into the cell. If one or more of the genes are already endogenous to the microbe, it can be used as is, although improvement in yield can usually be made by overexpressing an endogenous enzyme and control over induction of gene expression is also usually beneficial.

There are many examples of enzymes that can be used herein, and Table 1 provides some examples. Additional enzymes can be found by homology search, by curation at the various databases, by EC number, etc.

The process involves performing traditional cultures using industrial organisms (such as E. coli, S. cerevisiae, or Pichia pastoris) that convert various carbon sources (such as glucose, xylose, or glycerol) into chemical products through the operation of the modified enzymes and pathways described herein. These organisms are considered workhorses of modern biotechnology, and are easy to genetically engineer, and scale up for industrial production levels of desired products.

The pathways in a living system are generally made by transforming the microbe with an expression vector encoding one or more of the proteins catalyzing pathway steps, but the genes can also be added to the chromosome by recombineering, homologous recombination, and similar techniques. Where the needed protein is endogenous, as is the case in some instances (e.g., FAS enzymes or beta oxidation enzymes), it may suffice as is, but it is usually overexpressed using an inducible promoter for better functionality and user-control over the level of active enzyme. Deletions are made as described herein, or by any other method. Herein, we had a number of high succinate strains we could start with and so little deletion engineering was needed, although the fumA, fumB and fumC mutations were generated using the one-step inactivation method of Datsenko and Wanner (2000).

As used herein, the expressions "microorganism," "microbe," "strain," and the like may be used interchangeably and all such designations include their progeny. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

As used herein, the expressions "cell", "cell line" and "cell culture" are used interchangeably and all such designations include progeny. Thus, the words "cells" and similar designations include the primary subject cell and cultures derived therefrom without regard for the number of generation. It is also understood that all progeny may not be precisely identical in DNA content, due to deliberate or inadvertent mutations that arise after engineering is concluded. Mutant progeny that have the same function or biological activity as screened for in the originally transformed cell are included. Where distinct designations are intended, it will be clear from the context. Furthermore, reference to "a" cell typically includes cultures of that cell, which is common usage in the art.

As used herein, reference to a "cell" is generally understood to include a culture of such cells, as the work described herein is done in cultures having $10^{9-15}$ cells.

As used herein, "growing" cells used it its art accepted manner, referring to exponential growth of a culture of cells, not the few cells that may not have completed their cell cycle at stationary phase or have not yet died in the death phase or after harvesting.

As used in the claims, "homolog" means an enzyme with at least 40% identity to one of the listed sequences and also having the same general catalytic activity. While higher identity (60%, 70%, 80%) and the like may be preferred, it is typical for bacterial sequences to diverge significantly (40-60%), yet still be identifiable as homologs, while mammalian species tend to diverge less (80-90%).

Reference to proteins herein can be understood to include reference to the gene encoding such protein. Thus, a claimed "permease" protein can include the related gene encoding that permease. However, it is preferred herein to refer to the protein by standard name per ecoliwiki or HUGO since both enzymatic and gene names have varied widely, especially in the prokaryotic arts.

Once an exemplary protein is obtained, many additional examples of proteins with similar activity can be identified by BLAST search. Further, every protein record is linked to a gene record, making it easy to design overexpression vectors. Many of the needed enzymes are already available in vectors, and can often be obtained from cell depositories or from the researchers who cloned them. But, if necessary, new clones can be prepared based on available sequence information using RT-PCR techniques. Thus, it should be easily possible to obtain all of the needed enzymes for overexpression.

Generally speaking we have referenced protein names herein and included EC numbers for accurate identification, but it is understood that a change in protein activity can of course be effected by changing the gene. This provides clarity since the gene nomenclature can be widely divergent in bacteria, but the proteins are defined by their activities and EC numbers.

Once an exemplary protein is obtained, e.g., in *E. coli*, which is completely sequenced and which is the workhorse of genetic engineering and bioproduction, many additional examples proteins of similar activity can be identified by BLAST search. Further, every protein record is linked to a gene record, making it easy to design expression or overexpression vectors. Many of the needed enzymes are already available in vectors, and can often be obtained from cell depositories or from the researchers who cloned them. But, if necessary, new clones can be prepared based on available sequence information using RT-PCR techniques or chemical synthesis. Thus, it should be easily possible to obtain all of the needed enzymes for overexpression.

Another way of finding suitable proteins/genes for use in the invention is to consider other enzymes with the same EC number, since these numbers are assigned based on the reactions performed by a given enzyme. An enzyme that thus be obtained, e.g., from AddGene or from the author of the work describing that enzyme, and tested for functionality as described herein. In addition, many sites provide lists of proteins that all catalyze the same reaction.

Understanding the inherent degeneracy of the genetic code allows one of ordinary skill in the art to design multiple nucleotides that encode the same amino acid sequence. NCBI provides codon usage databases for optimizing DNA sequences for protein expression in various species. Using such databases, a gene or cDNA may be "optimized" for expression in *E. coli*, or other bacterial species using the codon bias for the species in which the gene will be expressed.

The pathways in a living system are generally made by transforming the microbe with an expression vector (preferably an inducible one) encoding one or more of the proteins, but the genes can also be added to the chromosome by recombineering, homologous recombination, and similar techniques. Where the needed protein is endogenous, as is the case in some instances, it may suffice as is, but it is usually overexpressed using an inducible promoter for better functionality and user-control over the level of active enzyme.

The term "endogenous" or "native" means that a gene originated from the species in question, without regard to subspecies or strain, although that gene may be naturally or intentionally mutated, or placed under the control of a promoter that results in overexpression or controlled expression of said gene. Thus, genes from Clostridia would not be endogenous to *Escherichia*, but a plasmid expressing a gene from *E. coli* or would be considered to be endogenous to any genus of *Escherichia*, even though it may now be overexpressed.

"Expression vectors" are used in accordance with the art-accepted definition of a plasmid, virus or other propagatable sequence designed for protein expression in cells. There are thousands of such vectors commercially available, and typically each has an origin of replication (ori); a multiple cloning site; a selectable marker; ribosome binding sites; a promoter and often enhancers; and the needed termination sequences. Most expression vectors are inducible, although constitutive expressions vectors also exist.

As used herein, "inducible" means that gene expression can be controlled by the hand-of-man, by adding e.g., a ligand to induce expression from an inducible promoter. Exemplary inducible promoters include the lac operon, inducible by IPTG, the yeast AOX1 promoter inducible with methanol, the strong LAC4 promoter inducible with lactate, and the like. Low level of constitutive protein synthesis may occur even in expression vectors with tightly controlled promoters.

As used herein, an "integrated sequence" means the sequence has been integrated into the host genome, as opposed to being maintained on an expression vector. It will still be expressible, and preferably is inducible as well.

Initial cloning experiments may have proceeded in *E. coli* for convenience since most of the required genes were already available in plasmids suitable for bacterial expression, but the addition of genes to bacteria is of nearly universal applicability. Indeed, since recombinant methods were invented in the 70's and are now so commonplace, even school children perform genetic engineering experiments using bacteria. Such species include e.g., *Bacillus, Streptomyces, Azotobacter, Trichoderma, Rhizobium, Pseudomonas, Micrococcus, Nitrobacter, Proteus, Lactobacillus, Pediococcus, Lactococcus, Salmonella*, and *Streptococcus*, or any of the completely sequenced bacterial species. Indeed, thousands of bacterial genomes have been completely sequenced, and this information greatly simplifies both the generation of vectors encoding the needed genes, as well as the planning of a recombinant engineering protocol. Such species are listed along with links at http://en.wikipedia.org/wiki/List_of_sequenced_bacterial_genomes, incorporated by reference herein in its entirety for all purposes.

Additionally, yeast, such as *Saccharomyces*, are a common species used for microbial manufacturing, and many species can be successfully transformed. Indeed, yeast are already available that express recombinant thioesterases and the reverse beta oxidation pathway has also been achieved in yeast. Other species include but are not limited to *Candida, Aspergillus, Arxula adeninivorans, Candida boidinii, Hansenula polymorpha (Pichia angusta), Kluyveromyces lactis, Pichia pastoris*, and *Yarrowia lipolytica*, to name a few.

It is also possible to genetically modify many species of algae, including e.g., *Spirulina, Apergillus, Chlamydomonas, Laminaria japonica, Undaria pinnatifida, Porphyra, Eucheuma, Kappaphycus, Gracilaria, Monostroma, Enteromorpha, Arthrospira, Chlorella, Dunaliella, Aphanizomenon, Isochrysis, Pavlova, Phaeodactylum, Ulkenia, Haematococcus, Chaetoceros, Nannochloropsis, Skeletonema, Thalassiosira*, and *Laminaria japonica*, and the like. Indeed, the microalga *Pavlova lutheri* is already being used as a source of economically valuable docosahexaenoic (DHA) and eicosapentaenoic acids (EPA), and *Crypthecodinium cohnii* is the heterotrophic algal species that is currently used to produce the DHA used in many infant formulas.

Furthermore, a number of databases include vector information and/or a repository of vectors and can be used to choose vectors suitable for the chosen host species. See e.g., AddGene.org which provides both a repository and a searchable database allowing vectors to be easily located and obtained from colleagues. See also Plasmid Information Database (PlasmID) and DNASU having over 191,000 plasmids. A collection of cloning vectors of *E. coli* is also kept at the National Institute of Genetics as a resource for the biological research community. Furthermore, vectors (including particular ORFS therein) are usually available from colleagues. Each of these databases is incorporated by reference herein in its entirety for all purposes.

The enzymes can be added to the genome or via expression vectors, as desired. Preferably, multiple enzymes are expressed in one vector or multiple enzymes can be combined into one operon by adding the needed signals between coding regions. Further improvements can be had by overexpressing one or more, or even all of the enzymes, e.g., by adding extra copies to the cell via plasmid or other vector. Initial experiments may employ one or more expression plasmids hosting 3 or more ORFs for convenience, but it may be preferred to insert operons or individual genes into the genome for stability reasons. Often chemically synthesized genes encoding the gene of interest can be used based on the sequence available in databases.

Still further improvements in yield can be made by removing competing pathways, such as those pathways for making e.g., acetate, formate, ethanol, and lactate, and it is already well known in the art how to reduce or knockout these pathways. See e.g., the inventors prior patents.

In calculating "% identity" the unaligned terminal portions of the query sequence are not included in the calculation. The identity is calculated over the entire length of the reference sequence, thus short local alignments with a query sequence are not relevant (e.g., % identity=number of aligned residues in the query sequence/length of reference sequence). Alignments are performed using BLAST homology alignment as described by Tatusova T A & Madden T L (1999) FEMS Microbiol. Lett. 174:247-250, and available through the NCBI website. The default parameters were used, except the filters were turned OFF.

The terms "operably associated" or "operably linked," as used herein, refer to functionally coupled nucleic acid sequences.

As used herein, "engineered" means an organism being recombinantly modified to change its genetics in a particular way to achieve a particular result.

As used herein "recombinant" or "recombinant engineering" is relating to, derived from, or containing genetic material intentionally modified by the hand of man. In other words, the genetics were intentionally manipulated in some way.

By "metabolically modified" we refer to random mutagenesis and selective pressure to evolve an organism in a desired direction. Such procedures are often employed after a recombinant engineering step to further improve production of a desired product.

"Reduced activity" or "inactivation" or "down-regulated" is defined herein to be at least a 75% reduction in protein activity, as compared with an appropriate control species. Preferably, at least 80, 85, 90, 95% reduction in activity is attained, and in the most extreme embodiment, the activity is eliminated (100%). Proteins can be inactivated with inhibitors, by mutation, or by suppression of expression or translation, and the like.

The terms "disruption" as used herein, refer to cell strains in which the native gene or promoter is mutated, deleted, interrupted, or down regulated in such a way as to decrease the activity of the protein at least 90% over the wild type un-disrupted protein. A gene or protein can be completely (100%) reduced by "knockout" or removal of the entire genomic DNA sequence. A reduced expression gene or protein can be represented by the − symbol. A "knockout" or "null" mutant can be represented by the A symbol.

Use of a frame shift mutation, early stop codon, point mutations of critical residues, or deletions or insertions, and the like, can completely inactivate (100%) gene product by completely preventing transcription and/or translation of active protein.

In general, deletion and reduction of gene activity is to be assayed by a reduction in enzymatic activity, not mRNA levels.

"Overexpression" or "overexpressed" is defined herein to be at least 150% of protein activity as compared with an appropriate control species or as having detectable expression of a gene not normally present in that host. Overexpression can be achieved by mutating the protein to produce a more active form or a form that is resistant to inhibition, by removing inhibitors, or adding activators, and the like. Overexpression can also be achieved by removing repressors, adding multiple copies of the gene to the cell, or upregulating the endogenous gene, and the like. An overexpressed gene can be represented by the + symbol, e.g., PYC+. In contrast, "expression" refers to normal levels of activity or better. In general, overexpression is to be assayed by an increase in enzymatic activity, not mRNA levels. Where needed, downstream production of product can be assayed if appropriate.

Acid and base forms of a molecule are used interchangeably herein, thus use of butyrate is intended to and does include butanoic acid.

NAD+ and NADH are used interchangeably herein, since the reactions involved convert one to the other. Likewise, NADP+ and NADPH are used interchangeably.

An "NAPDH-dependent" enzyme relies on NADPH as a cofactor, whereas an "NADH-dependent" enzyme uses NADH. An "NA(P)DH-dependent" enzyme can use either.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention.

The following abbreviations are used herein:

| ABBREVIATION | TERM |
|---|---|
| | alkene-mono-oxygenase |
| | trans-epoxysuccinate hydrolase (EC 3.3.2.4) (J Biol Chem. 1969 Apr 25; 244(8): 2078-84, incorporated by reference herein in its entirety for all purposes). |
| | succinyl-coenzyme A reductase (Arch Biochem Biophys. 2016 Apr 15; 596: 138-48; J Bacteriol. 1996 Feb; 178(3): 871-80, incorporated by reference herein in its entirety for all purposes. |
| AckA | Acetate Kinase P0A6A3 |
| Ackpta | also AckA-PTA - can mutate either or both genes in this operon |
| ACP | acyl carrier protein |
| adhE | Aldehyde-alcohol dehydrogenase P0A9Q7 |
| AMP | Ampicillin resistance |
| AspA | Aspartase aka Aspartate ammonia-lyase P0AC38 (*E. coli*); D3FYK2 (*Bacillus*) |
| CmR | chloramphenicol resistant gene |
| CoA | Coenzyme A |
| CRP | cyclic AMP receptor protein |
| fumA | fumarate hydratase class 1 P0AC33 |
| fumB | Fumarate hydratase class I, anaerobic P14407 |
| fumC | Fumarate hydratase class II P05042 |
| iclR | Transcriptional repressor - regulates glyoxylate bypass operon (aceBAK), which encodes isocitrate lyase, malate synthase as well as isocitrate dehydrogenase kinase/phosphorylase P16528 |
| IPTG | Isopropyl thiogalactoside |
| KM | Kanamycin resistance |
| Lacl | Lac operon repressor |
| LB media | Luria Broth media, commercially available |
| ldhA | L-lactate dehydrogenase A chain P00338 |
| M9 media | M9 minimal media, commercially available |
| mdh | Malate dehydrogenase P61889 |
| nadA | Quinolinate synthase A P11458 |
| nadB | L-aspartate oxidase P10902 |
| ori | origin of replication |
| panD | Aspartate 1-decarboxylase P9WIL3 (*E. coli*); P65662 (*Salmonella*); A0RBZ4 (*Bacillus*) |
| Pgm | Phosphoglucomutase |
| Pta | Phosphate acetyltransferase P0A9M8 |
| Pyc | Pyruvate carboxylase (P32327 yeast); Q9KWU4 (*Bacillus*); Q9RAT6 (*Lactococcus*) |
| Rrnb T1 terminator | terminator region from the *Escherichia coli* rrnB gene |
| rutE | Malonic semialdehyde reductase P75894 |
| SAD | succinate-semialdehyde dehydrogenase P76149 |
| SSDH | succinate-semialdehyde dehydrogenase EC 1.2.1.16 (J. Bacteriol. February 1996 vol. 178 no. 3 871-880, incorporated by reference herein in its entirety for all purposes) |
| SSR | succinic semialdehyde reductase (J. Bacteriol. February 1996 vol. 178 no. 3 871-880, incorporated by reference herein in its entirety for all purposes). |
| sucC | succinate CoA ligase (EC 6.2.1.5) P0A836 |
| TE | Thioesterase |
| Trc promoter | A Strong *E. coli* promoter hybrid between the trp (tryptophan) and lac UV5 (variant of the wild type *Escherichia coli* lac core promoter) promoters |

The invention includes any one or more of the following embodiment(s), in any combination(s) thereof:

A method of making a succinate-derived product, comprising:
growing an engineered bacteria in a culture medium;
 wherein said bacteria was engineered to produce more succinate than a control cell that is not so engineered; and
 wherein said bacteria was engineered to overexpress one or more enzymes to convert succinate to a succinate-derived product as compared with a control cell that is not so engineered;
allowing said bacteria to anaerobically make succinate;
allowing said bacteria to aerobically convert succinate to a succinate-derived product; and
isolating said succinate-derived product from said bacteria, said medium, or both.
Any method herein, wherein said bacteria has reduced activity of i) ldhA, ii) adhE, iii) iclR and iv) ackA or pta or ackA-pta, and v) one or more fumarase enzymes.
Any method herein, wherein said bacteria has a deletion of i) ldhA, ii) adhE, iii) iclR and iv) ackA or pta or ackA-pta, and v) one or more fumarase enzymes.
Any method herein, wherein said bacteria has a deletion in fumAC or fumAC and fumB.

-continued

Any method herein, wherein said bacteria comprises:
a deletion of i) ldhA, ii) adhE, iii) iclR and iv) ackA or pta or ackA-Pta and v) one or more fumarase enzymes; and
overexpressed aspartase.

Any method herein, wherein said bacteria comprises:
a deletion of i) ldhA, ii) adhE, iii) iclR and iv) ackA or pta or ackA-Pta and v) one or more fumarase enzymes; and
overexpressed aspartase and nadA and nadB.

Any method herein, wherein said bacteria comprises:
a deletion of i) ldhA, ii) adhE, iii) iclR and iv) ackA or pta or ackA-Pta and v) one or more fumarase enzymes; and
overexpressed aspartase and panD.

Any method herein, wherein said bacteria comprises
a deletion of i) ldhA, ii) adhE, iii) iclR and iv) ackA or pta or ackA-Pta and v) one or more fumarase enzymes; and
optionally overexpressed pyruvate carboxylase;
one or more overexpressed enzymes selected from nadA or nadB or aspartase or panD or succinate CoA ligase (EC 6.2.1.5) or succinate-semialdehyde dehydrogenase or succinate semialdehyde reductase or malonic semialdehyde reductase or succinic semialdehyde reductase or succinyl-coenzyme A reductase or succinyl-CoA ligase or trans-epoxysuccinate hydrolase (EC 3.3.2.4) or alkene-mono-oxygenase.

Any method herein, wherein said succinate-derived product is aspartic acid, beta-alanine, tartaric acid, epoxysuccinate, malate, or quinolinic acid.

An engineered bacteria having reduced activity of i) ldhA, ii) adhE, iii) iclR and iv) ackA or pta or ackA-Pta and v) one or more fumarase enzymes.

Any bacteria herein, plus overexpressed pyruvate carboxylase.

Any bacteria herein, plus overexpressed pyruvate carboxylase plus one or more overexpressed enzymes selected from nadA or nadB or aspartate or panD or succinate CoA ligase (EC 6.2.1.5) or succinate-semialdehyde dehydrogenase or malonic semialdehyde reductase or succinic semialdehyde reductase or succinyl-coenzyme A reductase, or succinyl-CoA ligase or trans-epoxysuccinate hydrolase (EC 3.3.2.4) or alkene-mono-oxygenase.

Any bacteria herein, plus one or more overexpressed enzymes selected from nadA or nadB or aspartase or panD or succinate CoA ligase (EC 6.2.1.5) or succinate-semialdehyde dehydrogenase or malonic semialdehyde reductase or succinic semialdehyde reductase or succinyl-coenzyme A reductase, or succinyl-CoA ligase or trans-epoxysuccinate hydrolase (EC 3.3.2.4) or alkene-mono-oxygenase.

An engineered bacteria having reduced activity of i) ldhA, ii) adhE, iii) iclR and iv) ackA or pta or ackA-Pta and v) one or more fumarase enzymes, plus overexpressed pyruvate carboxylase plus overexpressed aspartase and i) nadA and nadB or ii) panD.

An engineered bacteria having:
reduced activity one or more fumarase enzymes; and
overexpressed aspartase plus overexpressed nadA and nadB and able to convert succinate to quinolenic acid; or
overexpressed aspartase plus overexpressed panD and able to convert succinate to beta alanine.

An engineered bacteria having a deletion in fumAC and overexpressed aspartase.
An engineered bacteria having a deletion in fumABC and overexpressed aspartase.

A method of making a succinate-derived product, comprising:
co-culturing two strains of engineered bacteria:
    wherein a first bacteria was engineered to produce more succinate than a control cell that is not so engineered; and
    wherein a second bacteria was engineered to overexpress one or more enzymes to convert succinate to a succinate derived product;
allowing said first bacteria to produce succinate; and
allowing said second bacteria to convert said succinate to a succinate-derived product; and
isolating said succinate-derived product from said second bacteria, said medium, or both.

Any method herein, wherein said first bacteria comprises having reduced activity of i) ldhA, ii) adhE, iii) iclR and iv) ackA or pta or ackA-Pta and overexpressed PYC.

Any method herein, wherein said second bacteria comprises reduced fumarase and overexpressed aspartase.

Any method herein, wherein said second bacteria comprises reduced fumarase plus one or more overexpressed enzymes selected from nadA or nadB or aspartase or panD or succinate CoA ligase (EC 6.2.1.5) or succinate-semialdehyde dehydrogenase or malonic semialdehyde reductase or succinic semialdehyde reductase or succinyl-coenzyme A reductase, or succinyl-CoA ligase or trans-epoxysuccinate hydrolase (EC 3.3.2.4) or alkene-mono-oxygenase.

A method of making a succinate-derived product, comprising:
a) growing an engineered bacteria in a culture medium;
b) wherein said bacteria was engineered to produce more succinate than a control cell that is not so engineered; and
c) wherein said bacteria was engineered to overexpress one or more enzymes to convert succinate to a succinate-derived product as compared with a control cell that is not so engineered;
d) allowing said bacteria to make succinate under anaerobic conditions;
e) allowing said bacteria to convert succinate to a succinate-derived product under aerobic conditions; and f) isolating said succinate-derived product from said bacteria, said medium, or both.

An engineered bacteria having reduced activity of i) ldhA, ii) adhE, iii) iclR and iv) ackA or pta or ackA-Pta and v) one or more fumarase enzymes, plus overexpressed pyruvate carboxylase.

The above experiments are repeated in *Bacillus subtilis*. The same genes can be used, especially since *Bacillus* has no significant codon bias. A protease-deficient strain like WB800N is preferably used for greater stability of heterologous protein. The *E. coli*-*B. subtilis* shuttle vector pMTLBS72 exhibiting full structural stability can be used to move the genes easily to a more suitable vector for *Bacillus*. Alternatively, two vectors pHT01 and pHT43 allow high-level expression of recombinant proteins within the cytoplasm. As yet another alternative, plasmids using the theta-mode of replication such as those derived from the natural plasmids pAMβ1 and pBS72 can be used. Several other suitable expression systems are available. Since the FAS genes are ubiquitous metabolic genes, the invention is predicted to function in *bacillus*.

The following references are incorporated by reference in their entirety for all purposes:

All GenBank, UniProt, Kegg, etc. accession numbers and the data located therein are incorporated by reference herein in their entireties for all purposes. A person of ordinary skill in the art will be able to locate the relevant database, and access the gene/enzyme information stored therein, as well as links to other enzymes in the family.

U.S. Pat. No. 7,223,567 Mutant *E. coli* strain with increased succinic acid production U.S. Pat. No. 7,709,261 Recycling system for manipulation of intracellular NADH availability.

U.S. Pat. No. 7,901,924 Increased bacterial CoA and acetyl-CoA pools.

U.S. Pat. No. 7,927,859 High molar succinate yield bacteria by increasing the intracellular NADH availability U.S. Pat. No. 8,236,525 Reduced phosphotransferase system activity in bacteria.

U.S. Pat. No. 8,486,686 Large scale microbial culture method.

U.S. Pat. No. 8,709,753 Native NAD-dependent GAPDH replaced with NADP-dependent GAPDH plus NADK.

U.S. Pat. No. 8,795,991 Increasing bacterial succinate productivity.

Albright F. & Schroepfer G. J. Jr, L-trans-2,3-epoxysuccinate. A new substrate for fumarase, Biochem Biophys Res Commun. 40, 661-6 (1970).

Allen, R. H.; Jacoby, W. B., Tartaric Acid Metabolism: Synthesis With Tartrate Epoxidase, J. Biol. Chem. 244, 2078-2084 (1969).

Balzer G. J., Metabolic engineering of *Escherichia coli* to minimize byproduct formate and improving succinate productivity through increasing NADH availability by heterologous expression of NAD(+)-dependent formate dehydrogenase, Metab Eng. 20:1-8 (2013).

Buck, D., Cloning and expression of the succinyl-CoA synthetase genes of *Escherichia coli* K12, J. Gen. Microbiol. 132: 1753-1762 (1986).

Datsenko K. A. & Wanner B. L., One-step inactivation of chromosomal genes in *Escherichia coli* K-12 using PCR products, PNAS 97(12):6640-5 (2000).

Gokarn, R. R., et al., Expression of pyruvate carboxylase enhances succinate production in *Escherichia coli* without affecting glucose uptake rate. Biotech. Let. 1998, 20, 795-798.

Kockelkorn D. & Fuchs G. Malonic semialdehyde reductase, succinic semialdehyde reductase, and succinyl-coenzyme A reductase from *Metallosphaera sedula*: enzymes of the autotrophic 3-hydroxypropionate/4-hydroxybutyrate cycle in Sulfolobales., J. Bacteriol. 191:6352-6362 (2009).

Nolte, J. C., et al., Novel Characteristics of Succinate Coenzyme A (Succinate-CoA) Ligases: Conversion of Malate to Malyl-CoA and CoA-Thioester Formation of Succinate Analogues In Vitro, Applied and Environmental Microbiology, 80: 166-176 (2014).

Lin H, Vadali R V, et al., Increasing the acetyl-CoA pool in the presence of overexpressed phosphoenolpyruvate carboxylase or pyruvate carboxylase enhances succinate production in *Escherichia coli*. Biotechnol Prog. 20(5):1599-604 (2004).

Lin H., et al., Genetic reconstruction of the aerobic central metabolism in *Escherichia coli* for the absolute aerobic production of succinate. Biotechnol Bioeng. 89(2):148-56 (2005A).

Lin H., et al., Metabolic engineering of aerobic succinate production systems in *Escherichia coli* to improve process productivity and achieve the maximum theoretical succinate yield, Metab Eng. 7(2):116-27 (2005B).

Lin H, et al., Effect of Sorghum vulgare phosphoenolpyruvate carboxylase and *Lactococcus lactis* pyruvate carboxylase coexpression on succinate production in mutant strains of *Escherichia coli*. Appl Microbiol Biotechnol. 67(4):515-23 (2005C).

Ling, E. T. M., et al. Accumulation of 1-trans-2,3-Epoxysuccinic Acid and Succinic Acid by *Paecilomyces varioti*, Applied and Environ Microbiol 35: 1213-1215 (1978).

Martinez, I., et al., Metabolic impact of the level of aeration during cell growth on anaerobic succinate production by an engineered *Escherichia coli* strain, Metabolic Engineering 12: 499-509 (2010).

Sanchez, A. M., et al., Efficient succinate production from glucose through overexpression of pyruvate carboxylase in an *Escherichia coli* alcohol dehydrogense and lactate dehydrogenase mutant Biotechnol. Prog. 21: 358-365 (2005A).

Sanchez, A. M., et al., Novel pathway engineering design of the anaerobic central metabolic pathway in *Escherichia coli* to increase succinate yield and productivity. Metab. Eng. 7:229-39 (2005B).

Sanchez, A. M., et al., Batch culture characterization and metabolic flux analysis of succinate-producing *Escherichia coli* strains. Metabolic Engineering 8(3):209-26 (2006).

Shibata, H., et al., Purification, characterization, and immunological properties of fumarase from *Euglena gracilis* var. *bacillaris*, J. Bacteriol. 164, 762-768 (1985).

Tajima T., et al., Efficient aspartic acid production by a psychrophile-based simple biocatalyst, J Ind Microbiol Biotechnol. 42: 1319-24 (2015).

Tayeh, M. A. & Madigan, M. T., Malate dehydrogenases in phototrophic purple bacteria. Thermal stability, amino acid composition and immunological properties. Biochem J. 252(2): 595-600 (1988).

Vemuri et al. Effects of growth mode and pyruvate carboxylase on succinic acid production by metabolically engineered strains of *Escherichia coli*, Appl Environ Microbiol. 68(4):1715-27 (2002).

Vemuri, G. N., et al., Effect of growth mode and pyruvate carboxylase on succinic acid production by metabolically engineered strains of *Escherichia coli*. Appl Environ Microbiol. 6: 1715-1727 (2002).

Wilkoff, L. J. & Martin W. R., Studies on the biosynthesis of trans-1-epoxysuccinic acid by *Aspergillus fumigatus*, J. Biol. Chem. 238: 843-846 (1963).

TABLE 1

List of *E. coli* strains and plasmids

| Strain | Relevant genotype |
|---|---|
| MG1655* | Wild type *E. coli* (F⁻ λ⁻) |
| SBS110MG | ΔldhA ΔadhE |
| MBS410 | ΔldhA ΔadhE fumA::Km |
| MBS420 | ΔldhA ΔadhE fumB::Km |
| MBS412 | ΔldhA ΔadhE fumA fumB::Km |
| MBS432 | ΔldhA ΔadhE fumC fumB::Km |
| MBS406 | ΔldhA ΔadhE fumAC::Km |
| MBS426 | ΔldhA ΔadhE fumB fumAC::Km |
| MBS440 | Δmdh |
| SBS550MG | ΔadhE ΔldhA ΔiclR Δackpta |
| SBS550MG-Cms243 | ΔldhA ΔadhE ΔiclR Δackpta |
| SBS550MG-Cms243 (pHL413) | ΔldhA ΔadhE ΔiclR Δackpta (pyc+) |
| Plasmids | |
| pHL413 | Pyruvate carboxylase gene from *Lactococcus lactis* cloned in pTrc99A, Apʳ |

Any wild type bacteria can replace MG1655

We claim:

1. An engineered bacteria having
    a deletion of one or more fumarase enzymes and able to convert succinate to fumarate; and
    an overexpressed succinyl co-A ligase and succinical-semialdehyde dehydrogenase and succinic semialdehyde reductase (EC 1.1.1.B47) and able to convert succinate to 4-hydroxybutyrate.

2. The bacteria of claim 1, further comprising a) overexpressed pyruvate carboxylase and b) deletions of i) ldhA, ii) adhE, iii) iclR and iv) ackA or pta or ackA-pta.

3. A method of making a succinate-derived product, comprising:
    a. growing an engineered bacteria of claim 1 in a culture medium;
    b. allowing said bacteria to anaerobically make succinate;
    c. allowing said bacteria to convert succinate to a succinate-derived product under aerobic conditions; and
    d. isolating said succinate-derived product from said bacteria, said medium, or both.

4. The method of claim 3, wherein said bacteria has overexpressed pyruvate carboxylase.

5. The method of claim 4, wherein said bacteria has a deletion of i) ldhA, ii) adhE, iii) iclR and iv) ackA or pta or ackA-pta.

6. The method of claim 3, wherein said bacteria has a deletion of i) ldhA, ii) adhE, iii) iclR and iv) ackA or pta or ackA-pta.

7. The method of claim 3, wherein said bacteria comprises:
    a. overexpressed pyruvate carboxylase;
    b. a deletion of i) ldhA, ii) adhE, iii) iclR and iv) ackA or pta or ackA-pta; and
    c. said bacteria produces at least 1.2 moles of fumarate per mole of glucose.

* * * * *